United States Patent [19]

Profeta et al.

[11] 4,302,206
[45] Nov. 24, 1981

[54] APPARATUS AND PROCESS FOR ANALYSIS OF GASEOUS NITROGEN TRICHLORIDE

[75] Inventors: Barry P. Profeta, Lake Charles, La.; David A. Shaw, Johnstown, Pa.

[73] Assignee: Olin Corporation, New Haven, Conn.

[21] Appl. No.: 202,520

[22] Filed: Oct. 31, 1980

[51] Int. Cl.³ ............................................. G01N 21/33
[52] U.S. Cl. .................... 23/232 R; 356/51; 356/437; 422/83
[58] Field of Search .................... 23/232 R, 232 E; 422/83; 250/365; 356/51, 433, 437

[56] References Cited

U.S. PATENT DOCUMENTS 4,042,333  8/1977  Dell et al. ..................... 23/232 R

OTHER PUBLICATIONS

"The Absorption Spectra of Mono-, Di-, and tri--chloroamines and Some Aliphatic Derivatives" by W. S. Metcalf, 1942, pp. 148–150.
"Determination of Mono-, Di-, and Trichloramine by Ultraviolet Absorption Spectrophotometry" by Fred W. Czech et al., May, 1961, pp. 705–707.
"Laboratory and Developmental Work on Ultraviolet Light for Removal of Nitrogen Trichloride from Chlorine Gas" by Alonzo Farmer, Nov., 1962.
"Chemistry of Nitrogen Trichloride–A Review of the Literature" by Carl E. Vogler, Date and source unspecified.

Primary Examiner—Ronald Serwin
Attorney, Agent, or Firm—Donald F. Clements; James B. Haglind

[57]  ABSTRACT

Apparatus and process for analyzing the nitrogen trichloride concentration in gases containing it utilizing an ultraviolet light source. Unabsorbed filtered light collected from the sample at a wavelength of about 218 nm is compared with a standard at a wavelength of about 260 nm and the resultant is expressed in terms of nitrogen trichloride concentration.

15 Claims, 1 Drawing Figure

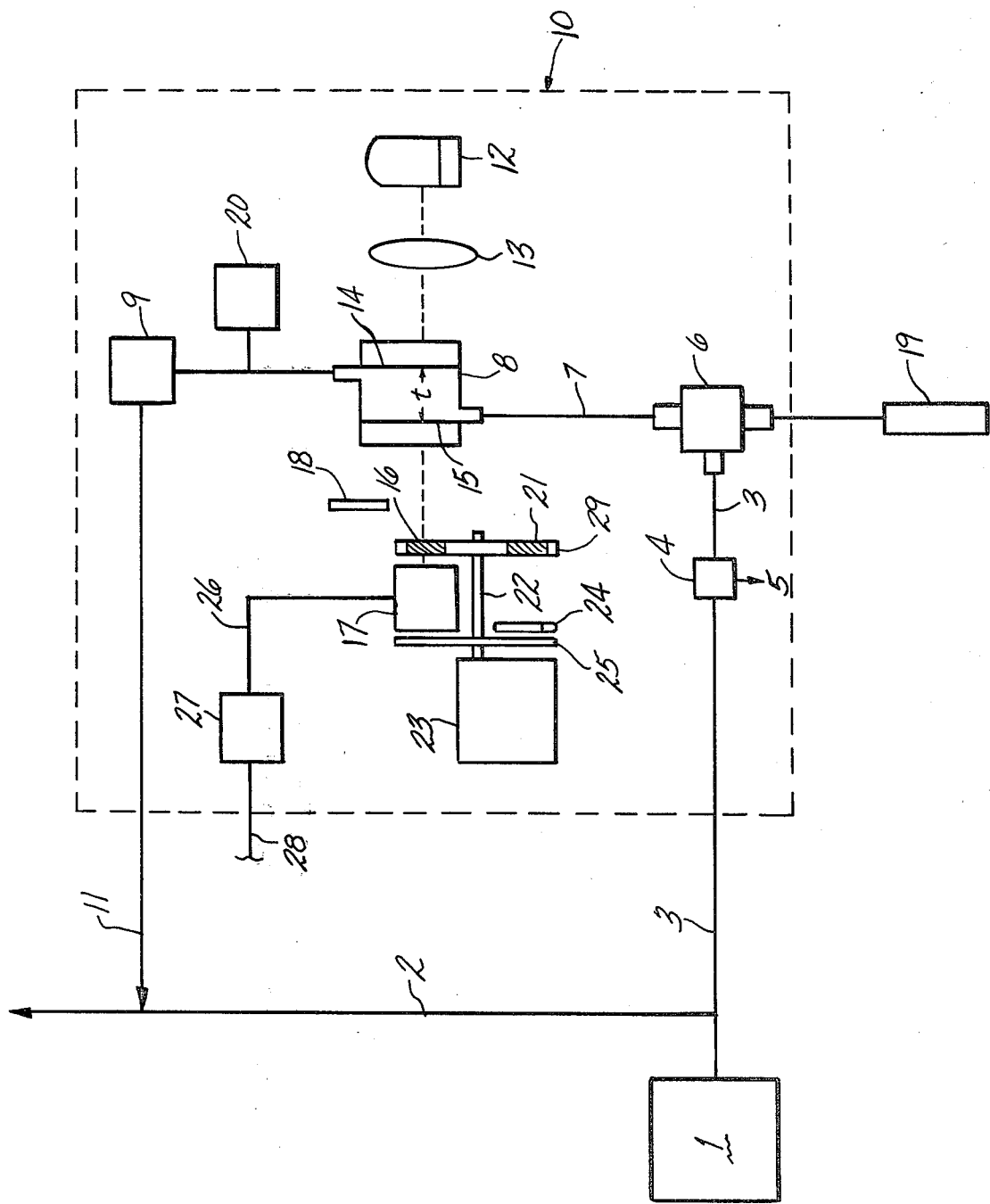

APPARATUS AND PROCESS FOR ANALYSIS OF GASEOUS NITROGEN TRICHLORIDE

This invention relates to an apparatus and process for analysis of gaseous nitrogen trichloride using ultraviolet light.

Numerous processes have been developed for the preparation of halogenated isocyanurates which are used extensively in the treatment of water, particularly in the purification of swimming pool water. Generally these processes all involve the use of cyanuric acid, alkali metal hydroxide, and halogen to prepare halogenated isocyanurates or their alkali metal salts. Typical compounds prepared in this manner are trichloroisocyanuric acid and sodium dichloroisocyanurate. During these reactions, there is a possibility of producing nitrogen trichloride and other halogenated amines as a byproduct. Gaseous nitrogen trichloride becomes a safety problem when it is present in the reactor system in concentrations above about 3 mole percent. Therefore, the reactions must be monitored with great care in order to prevent the buildup of nitrogen trichloride in the system.

One monitoring technique is described in U.S. Pat. No. 4,087,607 which issued May 2, 1978, in which a reaction slurry is analyzed by chromatographic technique to determine the nitrogen trichloride content. Once the concentration was determined, appropriate adjustment in the reaction process was made to reduce the buildup of nitrogen trichloride.

The use of ultraviolet absorption spectrophotometry to determine the concentration of nitrogen trichloride in certain solutions is disclosed in "The Absorption Spectra of Mono-, Di-, and Tri-chloroamines and Some Aliphatic Derivatives" by W. S. Metcalf from *Journal of the Chemical Society*, 1942, pages 148–150, and "Determination of Mono-, Di-, and Trichloramine by Ultraviolet Absorption Spectrophotometry" by Fred W. Czech et al, *Analytical Chemistry*, Vol. 33, No. 6, May 1961.

Although each of these techniques is capable of detecting the nitrogen trichloride concentration in slurries, considerable time is consumed in making the analysis on a wet basis. As a result, it may be too late to make any adjustment in the reaction system based upon the analysis because an explosion may occur before the analysis becomes available.

There is a pressing need in the isocyanurate industry for an apparatus and process for monitoring the concentration of nitrogen trichloride in gaseous streams on a continuous instantaneous basis in order that prompt corrective action can be taken before uncontrollable conditions arise in the reactor.

It is a primary object of this invention to provide an improved apparatus for analyzing the nitrogen trichloride concentration in gases containing it.

A further object of this invention is to provide an improved process for analyzing nitrogen trichloride concentration in gases containing it.

Still another object of this invention is to provide an improved method of calibrating a gas analyzer system utilizing ultraviolet light.

These and other objects of the invention will be apparent from the following detailed description thereof.

It has now been discovered that the foregoing objects are accomplished in an apparatus for analyzing gases for nitrogen trichloride utilizing ultraviolet light comprised of:

a. means for conveying a sample of gas to be analyzed for nitrogen trichloride to a gas analyzer system,
b. a cell having a fixed thickness through which said sample is passed during analysis,
c. a source of ultraviolet light capable of passing ultraviolet light across said thickness of said cell to a light detector means,
d. a first filter positioned between the cell and the light detector means, the filter permitting only light of about 218 nm from said cell to pass to the light detector means,
e. the light detector means being capable of measuring the amount of the sample light received from the filter and comparing it with a predetermined standard, and
f. means for expressing the sample light in terms of concentration of nitrogen trichloride in the sample.

The foregoing objects of the invention are further accomplished by the novel process of this invention for analyzing gases for nitrogen trichloride utilizing ultraviolet light which comprises:

a. passing a sample of gas to be analyzed for nitrogen trichloride from a gas generating reaction through a sample cell of predetermined fixed thickness along a flow path perpendicular to said fixed thickness,
b. simultaneously passing ultraviolet light from an ultraviolet source through the gas sample across said predetermined fixed thickness, whereby light energy at a wavelength of about 218 nm is absorbed by nitrogen trichloride in the gas sample passing through said cell, and the remaining unabsorbed light energy passes across said fixed thickness through said cell,
c. passing said remaining unabsorbed light energy through a first filter, whereby all of the remaining unabsorbed light energy other than about 218 nm is absorbed by the filter, the remaining filtered unabsorbed light of about 218 nm passes through said filter to a light detector means,
d. comparing said filtered unabsorbed light of about 218 nm in said light detector means with a predetermined standard of nitrogen trichloride concentration,
e. calculating the concentration of nitrogen trichloride in said gas sample, and
f. adjusting the reaction conditions in the gas generating reaction to maintain the concentration of nitrogen trichloride in subsequent gas samples within a predetermined range.

BRIEF DESCRIPTION OF THE DRAWING

The drawing shows in schematic form the apparatus and process for analyzing gas for nitrogen trichloride utilizing ultraviolet light.

One skilled in the art will recognize from a commercial standpoint the concentration of nitrogen trichloride in gaseous streams must be carefully controlled to avoid serious explosions. The apparatus and aprocess of this invention is not only effective in analyzing for nitrogen trichloride, but also can be utilized for analyzing gaseous streams for mono- and dichloroamines utilizing filters of appropriate wavelengths for these compounds. To simplify matters, the description and claims will be presented in terms of nitrogen trichloride, but those skilled in the art will recognize that the apparatus and process is also suitable for analyzing gaseous streams for other chlorinated amines.

The FIGURE shows reactor 1 used in the preparation of trichloroisocyanuric acid or other halogenated isocyanuric acid in which a gaseous byproduct stream is withdrawn comprised of clorine and nitrogen trichloride. Gas from reactor 1 is normally discharged through gas purge line 2 where it is either recycled to the process or otherwise disposed of. A sample of gas is withdrawn from purge line 2 through sample line 3 and conveyed to gas analyzer system 10, enclosed in the dotted lines. Sample line 3 conveys the gas sample to filter 4 where suspended solids and liquids are removed through waste line 5.

The clarified gas sample is conveyed through switching valve 6 and cell feed line 7 to cell 8. Conveying of the gas sample from purge line 2 is effected by means of aspirator 9 or other vacuum means. Pressure regulator 20 is preferably utilized to maintain constant pressure throughout gas analyzer system 10. The gas sample is conveyed from aspirator 9 through gas return line 11 to purge line 2.

Cell 8 has a predetermined fixed thickness perpendicular to the fixed flow path of gas sample through the cell. An ultraviolet light source 12 transmits ultraviolet light through lens 13 through first side 14 of cell 8 perpendicular to the path of flow of the gas sample, across said predetermined fixed thickness and out said second side 15 of cell 8. The predetermined fixed thickness t of cell 8 is between first side 14 and second side 15. A portion of light of about 218 nm is absorbed by any nitrogen trichloride in the sample in cell 8 and this portion does not pass through second side 15. The portion of unabsorbed light which passes through side 15 is conveyed to first filter 16 which absorbs all light other than light of about 218 nm. The remaining filtered unabsorbed light of about 218 nm is transmitted to light detector means 17 where it is compared with a predetermined standard for nitrogen trichloride concentration.

The predetermined standard is established in light detector means 17, by using as light, a reference wavelength of about 260 nm, a frequency at which substantially no light is absorbed by the sample. This is effected by utilizing a second filter 21 which is positioned between said second side 15 and said light detector means, after removal of said first filter. Said second filter removes all light except light of about 260 nm. In light detector means 17, the filtered unabsorbed light received by light detector means 17 at about 260 nm is then compared with the filtered unabsorbed light received at about 218 nm to obtain a unit of filtered unabsorbed light which is proportional to the quantitative concentration of nitrogen trichloride in the gas sample.

In order to obtain frequent continuous nitrogen trichloride analysis, first filter 16 and second filter 21 are placed in a suitable device such as a rotating wheel 29 which is secured by shaft 22 to motor 23. A mercury switch 24 operates from the magnetic wheel 25 positioned on shaft 22 to sense and electronically synchronize the position of the filters between second side 15 and light detector means 17.

Rotating wheel 29 may be rotated at any convenient rate, for example, from about 1800 rpm, which permits alternating first filter 16 and second filter 21 at the rate of 30 times per second. However, this rate can be varied depending upon the limits of the equipment employed. If desired, a beam splitter type of comparison can be employed in place of the rotating wheel 29.

Light detector means 17 is electrically connected through line 26 to activator 27 which is utilized to activate any number of desired systems (not shown) through activating line 28 for controlling the nitrogen trichloride concentration in the purge gases in purge line 2. When the concentration of nitrogen trichloride in the gas sample exceeds a predetermined limit, activator 27 can be utilized to control the rate of feed of reactants to reactor 1 or other reaction conditions. If desired, activator 27 can cause an alarm to be sounded when the concentration of nitrogen trichloride exceeds a predetermined limit and, if desired, the entire reaction can be terminated by appropriate action of activator 27.

Calibration of the light detector means 17 is effected by use of a span filter 18 which absorbs a portion of light at about 218 nm, corresponding to a concentration of nitrogen trichloride midway within the range of concentration of nitrogen trichloride being detected. In establishing the predetermined standard, aspirator 9 is used to evacuate gas sample from cell 8 and switching valve 6 is adjusted to convey a $NCl_3$-free gas from $NCl_3$-free gas source 19 to cell 8. Span filter 18 is positioned between second side 15 and first filter 16 and light detector means 17 collects the resulting unabsorbed light which it receives. Light detector means 17 is then calibrated to establish this amount of unabsorbed light as being equivalent to a concentration of nitrogen trichloride midway within the range of nitrogen trichloride concentrations being detected. After this standard is established, span filter 18 is moved out of position as shown in the drawing and switching valve 6 is positioned to convey gas samples from gas sample line 3 to cell feed line 7.

In the process of this invention, nitrogen trichloride gas of any convenient concentration can be analyzed. Generally the dangerous concentration of nitrogen trichloride is about 3 mole percent or more. As a result, span filter 18 used in the calibration of light detector means 17, is designed to absorb about 50 percent of the unabsorbed light at a wavelength of about 218 nm which passes through cell 8 over a nitrogen trichloride concentration range of from about 0.1 to about 5 mole percent.

One of the advantages of this invention is that a span filter rather than actual nitrogen trichloride standardized gases are used to calibrate light detector means 17. If desired, calibration of light detector means 17 is effected by feeding a series of gas samples of known nitrogen trichloride concentrations to cell 8 and recording in light detector means 17 the filtered unabsorbed light at about 218 nm. Although feasible, the latter technique is inconvenient and somewhat unreliable because of the instability of the nitrogen trichloride in the standard gas samples and because of the potential risk of explosion of the standard gas samples at the higher nitrogen trichloride concentrations. Therefore span filter 18 not only eliminates the risk of explosion during calibration, but also provides a reliable constant technique for standardizing the gas analyzer system 10.

A typical reaction which produces nitrogen trichloride is the reaction of cyanuric acid, sodium hydroxide, hypochlorous acid, and excessive amounts of chlorine to produce trichloroisocyanuric acid. Purge gas is withdrawn from the reactor having a typical analysis as follows:

| Component | Mole Percent |
| --- | --- |
| H₂O | 1.63 |
| Chlorine | 82.83 |
| Carbon Dioxide | 14.21 |
| Nitrogen Trichloride | 1.3 |

It is desired to maintain the nitrogen trichloride concentration in the purge gas below about 2 mole percent to avoid hazardous operating conditions and this can be effected easily by increasing the amount of chlorine gas used to purge the reactor off-gases from reactor 1. Those skilled in the art will recognize that the composition of the purge gas will vary from the above typical composition, depending upon the type of reaction used to generate the nitrogen trichloride containing gases.

Any energy source capable of generating polychromatic ultraviolet light may be used as ultraviolet light source 12. Typical suitable ultraviolet light analyzer systems which comprise a source of ultraviolet light 12, cell 8, and light detector means 17, are duPont's Model 400, Teledyne's Model 611, and Anacon's Model 207 which are presently available commercially. However, any suitable ultraviolet light analyzer system may be employed.

The quality of first filter 16, span filter 18 and second filter 21 greatly affect the precision and accuracy of the nitrogen trichloride analysis. For example, gaseous nitrogen trichloride absorbs light over a wavelength range of about 200 to about 250 nm with a peak at about 218 nm. It is preferred to use a first filter 16 having the narrowest range possible, for example, in the range from about 213 to about 223 nm. However, first filter 16, if capable of absorbing all light outside the range of from about 205 to about 230 nm could generally be used with some degree of qualitative analysis. Throughout the description and claims, for purpose of simplicity, the term "about 218 nm" includes the narrow range of from 213 to 223 nm as well as the broad range of from about 205 to about 230 nm.

The quality of span filter 18 will also determine the effectiveness of gas analyzer system 10. Span filter 18 is preferably designed to absorb approximately 50 percent of the light within the range of about 205 to about 230 nm at a nitrogen trichloride concentration range of about 0.1 to about 5 mole percent. However, the wavelength of span filter 18 could be increased to the range from about 200 to about 235 nm, but there may be some reduction in the effectiveness of the calibration of gas analyzer system 10.

In standardizing the gas analyzer system 10, second filter 21 is used which is capable of filtering out all light which has passed through the sample except the light at a wavelength of about 218 nm. Preferably second filter 21 filters out all light outside the range of from about 250 to about 270 nm. If desired, the range of unfiltered light passing through second filter 21 may be enlarged in the range from about 250 to about 280 nm but the efficiency of the gas analyzer system 10 is greatly reduced when second filter 21 has such a wide range of unabsorbed light.

The first predetermined thickness of the cell is established to provide an analysis over the range of concentration of nitrogen trichloride expected to be detected in the gas sample. For example, when the range of nitrogen trichloride concentration is from about 0 to about 5 mole percent, the fixed predetermined thickness is about 0.2 mm. If a smaller concentration range is desired, the fixed predetermined thickness t is increased and if a higher concentration range of nitrogen trichloride is desired, the fixed predetermined thickness t is decreased.

What is claimed is:

1. An apparatus for analyzing gases for nitrogen trichloride utilizing ultraviolet light comprised of:
   a. means for conveying a sample of gas to be analyzed for nitrogen trichloride to a gas analyzer system,
   b. cell having a fixed predetermined thickness through which said sample is passed during analysis,
   c. a source of ultraviolet light capable of passing ultraviolet light across said thickness through said cell to a light detector means,
   d. a first filter positioned between said cell and said light detector means, said filter permitting sample light of about 218 nm to pass to said light detector means,
   e. said light detector means being capable of measuring the amount of said sample light received from said filter and comparing it with a predetermined standard, and
   f. means for expressing said sample light in terms of concentration of nitrogen trichloride in said sample.

2. The apparatus of claim 1 wherein a second filter is positioned between said cell and said light detector means, said filter permitting light of about 260 nm to pass to said light detector means, wherein said light passing through said second filter is received by said light detector means then compared with the light received from said sample at about 218 nm, and means for expressing the resulting comparison as concentration of nitrogen trichloride in said sample.

3. The apparatus of claim 2 wherein said first filter and said second filter are positioned opposite each other on a rotating member, means are provided for rotating said filters between said cell and said light detector means, whereby said light detector means receives alternately light from said first filter followed by light from said second filter.

4. The apparatus of claim 3 wherein said first filter and said second filter are placed on a rotating wheel and said wheel is rotated by means of a motor drive.

5. The apparatus of claim 1, 2, 3, or 4 wherein the concentration of nitrogen trichloride is in the range from about 0.1 to about 100 mole percent.

6. The apparatus of claim 1, 2, 3, or 4 wherein the concentration of nitrogen trichloride is in the range of from about 0.1 to about 5 mole percent.

7. The apparatus of claim 1, 2, 3, or 4 wherein said gas analyzer system is provided with a third filter capable of absorbing a portion of light at about 218 nm, whereby calibration of said light detector means is effected by evacuating all NCl₃-containing gas from said cell and passing light from said ultraviolet light source through said cell and said third filter to said light detector means.

8. The apparatus of claim 4 wherein said gas analyzer means is provided with vacuum means for conveying said sample through said cell and out of said gas analyzer system.

9. The apparatus of claim 8 wherein said vacuum means is provided with a pressure regulator.

10. The apparatus of claim 9 having a switch means for either conveying said sample to said cell or for evacuating said gas from said cell.

11. The apparatus of claim 10 wherein said first filter and said second filter are placed on a rotating wheel and said wheel is rotated by means of a motor drive and a mercury switch senses and electronically synchronizes the position of said filter filter and said second filter.

12. The process for analyzing nitrogen trichloride in gases containing it which comprises:
   a. passing a sample of gas to be analyzed for nitrogen trichloride from a gas generating reaction through a sample cell of predetermined fixed thickness along a flow path perpendicular to said fixed thickness,
   b. simultaneously passing ultraviolet light from an ultraviolet source through the gas sample across said predetermined fixed thickness, whereby light energy at a wavelength of about 218 nm is absorbed by nitrogen trichloride in the gas sample passing through said cell, and remaining unabsorbed light energy passes across said fixed thickness through said cell,
   c. passing said remaining unabsorbed light energy through a first filter, whereby all of the remaining unabsorbed light energy other than about 218 nm is absorbed by the filter, the remaining filtered unabsorbed light of about 218 nm passes through said filter to a light detector means,
   d. comparing said filtered unabsorbed light of about 218 nm in said light detector means with a predetermined standard of nitrogen trichloride concentration,
   e. calculating the concentration of nitrogen trichloride in said gas sample, and
   f. adjusting the reaction conditions in the gas generating reaction to maintain the concentration of nitrogen trichloride in subsequent gas samples within a predetermined range.

13. The process of claim 12 wherein the concentration of nitrogen trichloride is in the range from about 0.1 to about 5 mole percent.

14. The process of claim 12 wherein calibration of said light detector means is effected by use of a span filter which filters out all light except light having a wavelength of about 218 nm.

15. The process of claim 12, 13, or 14 wherein said comparing is made by passing light at about 260 nm through said sample and absorbing in a filter all light outside of about 260 nm, and comparing the resulting ulfiltered, unabsorbed light at about 260 nm with the light received at about 218 nm.

* * * * *

UNITED STATES PATENT AND TRADEMARK OFFICE
CERTIFICATE OF CORRECTION

PATENT NO. : 4,302,206
DATED : November 24, 1981
INVENTOR(S) : Barry P. Profeta and David A. Shaw It is certified that error appears in the above-identified patent and that said Letters Patent are hereby corrected as shown below:

In Column 2, line 61, after "and" delete "aprocess" and insert --a process--.

In Column 3, line 6, delete "clorine" and insert --chlorine--.

In Column 7, Claim 11, line 5, after "said" (first occurrence) delete "filter" and insert --first--.

In Column 8, Claim 15, line 24, delete "ulfiltered" and insert --unfiltered--.

Signed and Sealed this

Sixth Day of April 1982

|SEAL|

Attest:

GERALD J. MOSSINGHOFF

Attesting Officer    Commissioner of Patents and Trademarks